(12) United States Patent
Vert-Wong

(10) Patent No.: US 10,548,908 B2
(45) Date of Patent: Feb. 4, 2020

(54) COMPOSITIONS AND METHODS FOR PREVENTING AND TREATING HETEROTOPIC OSSIFICATION AND PATHOLOGIC CALCIFICATION

(71) Applicant: Nostopharma, LLC, Bethesda, MD (US)

(72) Inventor: Ekaterina Vert-Wong, Potomac, MD (US)

(73) Assignee: Nostopharma, LLC, Bethesda, MD (US)

( * ) Notice: Subject to any disclaimer, the term of this patent is extended or adjusted under 35 U.S.C. 154(b) by 0 days.

(21) Appl. No.: 15/702,758

(22) Filed: Sep. 13, 2017

(65) Prior Publication Data

US 2018/0071319 A1 Mar. 15, 2018

Related U.S. Application Data

(60) Provisional application No. 62/395,374, filed on Sep. 15, 2016.

(51) Int. Cl.

| | | |
|---|---|---|
| *A61K 31/165* | (2006.01) | |
| *A61K 31/593* | (2006.01) | |
| *A61K 31/35* | (2006.01) | |
| *A61K 31/404* | (2006.01) | |
| *A61K 31/40* | (2006.01) | |
| *C12N 5/0775* | (2010.01) | |
| *A61K 31/47* | (2006.01) | |
| *A61K 45/06* | (2006.01) | |
| *A61K 31/22* | (2006.01) | |
| *A61K 31/4418* | (2006.01) | |
| *A61K 31/366* | (2006.01) | |
| *A61K 31/505* | (2006.01) | |
| *A23L 33/155* | (2016.01) | |
| *C12N 5/077* | (2010.01) | |

(52) U.S. Cl.
CPC .......... *A61K 31/593* (2013.01); *A23L 33/155* (2016.08); *A61K 31/22* (2013.01); *A61K 31/366* (2013.01); *A61K 31/40* (2013.01); *A61K 31/404* (2013.01); *A61K 31/4418* (2013.01); *A61K 31/47* (2013.01); *A61K 31/505* (2013.01); *A61K 45/06* (2013.01); *C12N 5/0654* (2013.01); *C12N 5/0663* (2013.01); *A61L 2400/02* (2013.01); *C12N 2500/05* (2013.01); *C12N 2500/38* (2013.01); *C12N 2501/315* (2013.01); *C12N 2501/36* (2013.01); *C12N 2501/41* (2013.01); *C12N 2501/999* (2013.01); *C12N 2506/1353* (2013.01)

(58) Field of Classification Search
CPC ..... A61K 31/165; A61K 31/593; A61K 31/35
USPC .............. 514/167, 460, 504, 577
See application file for complete search history.

(56) References Cited

U.S. PATENT DOCUMENTS

| | | |
|---|---|---|
| 4,851,400 A | 7/1989 | DeLuca et al. |
| 4,857,518 A | 8/1989 | DeLuca et al. |
| 4,891,364 A | 1/1990 | Kubodera et al. |
| 5,232,836 A | 8/1993 | Bouillon et al. |
| 5,446,035 A | 8/1995 | Neef et al. |
| 5,665,716 A | 9/1997 | Kirsch et al. |
| 5,700,791 A | 12/1997 | Steinmeyer et al. |
| 5,756,733 A | 5/1998 | Hesse et al. |
| 5,945,410 A | 8/1999 | DeLuca et al. |
| 6,013,814 A | 1/2000 | Hesse et al. |
| 6,043,385 A | 3/2000 | Barbier et al. |
| 6,124,276 A | 9/2000 | Miyamoto et al. |
| 6,277,837 B1 | 8/2001 | DeLuca, Jr. et al. |
| 6,291,516 B1 | 9/2001 | Dudek et al. |
| 6,359,152 B2 | 3/2002 | DeLuca et al. |
| 6,538,145 B2 | 3/2003 | Hatakeyama et al. |
| 6,683,108 B1 | 1/2004 | Baxler et al. |
| 7,074,777 B2 | 7/2006 | Kawase et al. |
| 7,112,579 B2 | 9/2006 | DeLuca et al. |
| 7,115,758 B2 | 10/2006 | Steinmeyer et al. |
| 7,211,680 B2 | 4/2007 | Steinmeyer et al. |
| 7,407,967 B2 | 8/2008 | Adams et al. |
| 7,659,421 B2 | 2/2010 | Terranova et al. |
| 7,741,298 B2 | 6/2010 | Altaba et al. |
| 7,985,744 B2 | 7/2011 | Morikawa et al. |
| 8,030,454 B2 | 10/2011 | Scales |
| 8,101,610 B2 | 1/2012 | Goldsmith et al. |
| 8,198,263 B2 | 6/2012 | Moras et al. |
| 8,273,747 B2 | 9/2012 | Brunton et al. |
| 8,410,601 B2 | 4/2013 | Samples |
| 8,486,400 B2 | 7/2013 | Dudek et al. |
| 8,530,456 B2 | 9/2013 | Peng et al. |
| 8,759,367 B2 | 6/2014 | Dahmane et al. |
| 8,778,927 B2 | 7/2014 | Dorsch et al. |
| 8,802,639 B2 | 8/2014 | Bumcrot |

(Continued)

FOREIGN PATENT DOCUMENTS

| | | |
|---|---|---|
| CA | 2979230 | 9/2017 |
| WO | WO 2007/136250 | 11/2007 |
| WO | PCT/US2018/021776 | 3/2018 |

OTHER PUBLICATIONS

International Search Report for PCT/US2018/21776 filed Mar. 9, 2018.

(Continued)

*Primary Examiner* — Raymond J Henley, III

(74) *Attorney, Agent, or Firm* — The Law Office of: Michael A. Sanzo, LLC

(57) ABSTRACT

The present invention is directed to compositions and methods for the prevention or treatment of treatment of heterotopic ossification, vascular calcification, or pathologic calcification.

44 Claims, 1 Drawing Sheet

Specification includes a Sequence Listing.

(56) References Cited

U.S. PATENT DOCUMENTS

| | | | |
|---|---|---|---|
| 8,835,648 | B2 | 9/2014 | Thomas et al. |
| 9,000,023 | B2 | 4/2015 | Hipskind et al. |
| 9,073,835 | B2 | 7/2015 | Ruat et al. |
| 9,096,686 | B2 | 8/2015 | de Sauvage et al. |
| 9,149,527 | B2 | 10/2015 | Fung et al. |
| 9,173,869 | B2 | 11/2015 | Guicherit et al. |
| 9,174,949 | B2 | 11/2015 | Vernier et al. |
| 9,216,964 | B2 | 12/2015 | Cheng et al. |
| 9,278,961 | B2 | 3/2016 | Gunzner et al. |
| 9,321,761 | B2 | 4/2016 | Gunzner-Toste et al. |
| 9,345,699 | B2 | 5/2016 | Tao et al. |
| 9,346,791 | B2 | 5/2016 | Liu et al. |
| 9,409,871 | B2 | 8/2016 | He et al. |
| 9,427,431 | B2 | 8/2016 | Beachy et al. |
| 10,456,409 | B2 | 10/2019 | Nostopharma |
| 2006/0240092 | A1* | 10/2006 | Breitenkamp ....... A61K 9/1075 424/450 |
| 2008/0066741 | A1* | 3/2008 | LeMahieu ............ A61M 11/041 128/200.21 |
| 2009/0163452 | A1* | 6/2009 | Schwartz ............... A61K 31/59 514/167 |
| 2009/0214474 | A1 | 8/2009 | Jennings |
| 2011/0081323 | A1 | 4/2011 | Kleinsek et al. |
| 2013/0116215 | A1* | 5/2013 | Coma .................. A61K 31/165 514/108 |
| 2014/0220154 | A1 | 8/2014 | Regard et al. |
| 2017/0088553 | A1 | 3/2017 | Grenier et al. |
| 2019/0175621 | A1 | 6/2019 | Nostopharma |

OTHER PUBLICATIONS

Written Opinion of the International Searching Authority for PCT/US2018/21776 filed Mar. 9, 2018.
Akers, et al., "Excipient-Drug Interactions in Parenteral Formulations," *J. Pharm. Sci.* 91(11):2283-2300 (Nov. 2002).
Baird, et al., "Prophylaxis of heterotopic ossification—an updated review," *Journal of Orthopaedic Surgery and Research* 4(12):1-8 (Apr. 2009).
Bakshi, et al., "Development of validated stability-indicating assay methods—critical review," *Journal of Pharmaceutical and Biomedical Anaylsis* 28(6):1011-1040 (Jun. 2002).
Boström, et al., "Bone Morphogenetic Protein Expression in Human Atherosclerotic Lesions," *J. Clin. Invest.* 91:1800-1809 (Apr. 1993).
Challa, et al., "Cyclodextrins in Drug Delivery: An Updated Review," *AAPS PharmSciTech* 6(2):E329-E57 (Oct. 2005).
Genc, et al., "Formulation of Nano Drug Delivery Systems," *Journal of Materials Science and Engineering A*, 132-137 (Jun. 2011).
Krishna, et al., "Pharmaceutical Development and Manufacturing of a Parenteral Formulation of a Novel Antitumor Agent," *AAPS PharmaSciTech* 2(3):39-47 (Aug. 2001).
Lambert, "Considerations in Developing a Target Product Profile for Parenteral Pharmaceutical Products," *AAPS PharmSciTech* 11(3):1476-1481 (Sep. 2010).
Merisko-Liversidge, et al., "Nanosizing for oral and parenteral drug delivery: A perspective on formulating poorly-water soluble compounds using wet media milling technology," *Advanced Drug Delivery Reviews* 63(3):427-440.
Palmieri, et al., "Inclusion of Vitamin-D2 in BetaCyclodextrin—Evaluation of Different Complexation Methods," *Drug Development and Industrial Pharmacy* 19(8):875-885 (published online Oct. 1993).
Piao, et al., "A review of the extraction and chromatographic determination methods for the analysis of parabens," *Journal of Chromatography B* 969:139-148 (Oct. 2014).
Plaisant, et al., "Inhibition of Hedgehog Signaling Decreases Proliferation and Clonogenicity of Human Mesenchymal Stem Cells," *PLoS One* 6(2):e16798 (Feb. 2011).
Regard, et al., "Activation of Hedgehog signaling by loss of GNAS causes hetertopic ossification," *Nature Medicine* 19(11):1505-1512 (Nov. 2013).
Sumi, et al., "Arsenic tioxide augments all-trans retinoic acid-induced differentiation of HL-60 cells," *Life Sciences* 149:42-50 (Mar. 2016).
Sun, et al., "Drug combination therapy increases successful drug repositioning," *Drug Discovery Today* 21(7):1189-1195 (Jul. 2016).
Tang, et al., "Vitamin D3 Inhibits Hedgehog Signaling and Proliferation in Murine Basal Cell Carcinomas," *Cancer Prevention research* 4(5):744-751 (May 2011).
Tsai, et al., "Identification of Bone Marrow-Derived Soluble Factors Regulating Human Mesenchymal Stem Cells for Bone Regeneration," *Stem Cell Report* 8:387-400 (Feb. 2017).
Yu, et al., "Understanding Pharmaceutical Quality by Design," *AAPS Journal* 16(4):771-783 (Jul. 2014).
Zaid, et al., "Compounding and Stability Evaluation of Atorvastatin Extemporaneous Oral Suspension Using Tablets or Pure Powder," *European Journal of Hospital Pharmacy* 24:157-161 (available online Jun. 2016).
Zhao, et al., "Foxp1/2/4 regulate endochondral ossifications a suppresser complex," *Dev. Biol.* 398:242-254 (Feb. 2015, available online Jul. 2014).
Albert, et al., "Interaction of hedgehog and Vitamin D signaling pathways in basal cell carcinomas," *Adv. Exp. Med. Biol.* 810:329 (2014).
Anfinsen, et al., "Severe Systemic Calciphylaxis in a Young Cat," *J. Vet. Intern. Med.* 28(4):1325-1330 (Jul.-Aug. 2014).
Asano, et al., "Fibrodysplasia Ossifications Progressiva-like Condition in a Cat," *J. Vet. Med. Sci.* 68(9):1003-1006 (Oct. 2006).
Baird, et al., "Prophylaxis of heterotopic ossification—an updated review," *J. Orthop. Surg. Res.* 4(12):1-8 (Apr. 2009).
Barry, et al., "Mesenchymal stem cells in joint disease and repair," *Nature Reviews Rheumatology* 9(10):584 (Oct. 2013).
Cooper, et al., "A defective response to Hedgehog signaling in disorders of cholesterol biosynthesis," *Nature Genetics* 33(4):508-513 (Apr. 2003).
Corcoran, et al., "Oxysterols stimulate Sonic hedgehog signal transduction and proliferation of medulloblastoma cells," *Proc. Natl. Acad. Sci. USA* 103(22):8408-8413 (May 2006).
Cortes, et al., "Accumulation of the Vitamin D Precursor Cholecalciferol Antagonizes Hedgehog Signaling to Impair Hemogenic Endothelium Formation," *Stem Cell Reports* 5:471-479 (Oct. 2015).
Eddy, et al., "Deficiency of the a-Subunit of the Stimulatory G Protein and Severe Extraskeletal Ossification," *J. Bone Miner. Res.* 15(11):2074-2083 (Nov. 2000).
Edwards, et al., "Heterotopic ossification in victims of the London 7/7 bombing," *J. R. Army Med. Corps.* 161:315 (2015).
Eisens IhIN, et al., "Post-Traumatic Heterotopic Ossification: an Old Problem in Need of New Solutions," *Jour. Ortho. Res.* 36(4):1061-1068 (Apr. 2018).
Kan, et al., "Dysregulation of Local Stem/Progenitor Cells as a Common Cellular Mechanism for Heterotopic Ossification," *Stem Cells* 2(1)7:150-156 (Jan. 2009).
Kan, et al., "BMP-dependent, injury-induced stem cell niche as a mechanism of heterotopic ossification," *Stem Cell Research & Therapy* 10:14 pp. 1-17 (published online Jan. 2019).
Kan, et al., "Evaluation of the Cellular Origins of Heterotopic Ossification," *Orthopedics* 37(5):329 -340 (May 2014).
Kan, et al., "Gli1-labeled adult mesenchymal stem/progenitor cells & hedgehog signaling contribute to endochondral heterotopic ossification," *Bone* 109:71-79 (Apr. 2018).
Kaplan, et al., "Heterotopic Ossificatio: Two Rare Forms and What They Teach Us," *J. Am. Acad. Orthop. Surg.* 2:288-296 (Oct. 1994).
King, "Post-traumatic ectopic calcification in the muscles of athletes: a review," *Br. J. Sports Med.* 32(4):287-290 (Dec. 1998).
Linder, et al., "A Functional and Putative Physiological Role of Calcitriol in Patchedl/Smoothened Interaction," *J. Biol. Chem.* 290(32):19614-19628 (Aug. 2015).
Lo, et al., Studies of Bone Morphogenetic Protein based Surgical Repair, *Adv. Drug Deliv. Rev.* 64(12)1277-1291 (Sep. 2012).
Mumcuoglu, et al., "How to use BMP-2 for clinical applications? A Review on pros and cons of existing delivery Strategies," *J. Transl. Sci.* 3(5):1-11 (Aug. 2017).

(56) References Cited

OTHER PUBLICATIONS

Pacifici, "Acquired and congenital forms of heterotopic ossification: new pathogenic insights and therapeutic opportunities," *Current Opinion in Pharmacology* 40:51-58 (Jun. 2018).
Shore, et al., "Inherited human diseases of heterotopic formation," *Nat. Rev. Rheumatol.* 6(9):518-527 (Sep. 2010).
Shore, et al., "A recurrent mutation in the BMP type 1 receptor ACVR1 causes inherited and sporadic fibrodysplasia ossificans progressiva," *Nat. Genet.* 38(5):525 (Epub Apr. 2006).
Siffert, "The Role of Alkaline Phosphate in Osteogenesis," *J. Exp. Med.* 93(5):415-429 (May 1951).
Stecca, et al., "Context-dependent Regulation of the GLI Code in Cancer by HEDGEHOG and Non-HEDGEHOG Signals," *J. Mol. Cell Biol.* 2(2):84-95 (Apr. 2010).
Tenenbaum, et al., "Differentiation of osteoblasts and formation of mineralized bone in vitro," *Calcified Tissue International* 34(1):76-79 (Dec. 1982).
Udupa, et al., "Treatment of Acute Promyelocytic Leukemia with Single Agent Arsenic Trioxide: Experience from Tertiary Care Center in India," *Indian J. Hematol. Blood Transfus.* 33(1):45-48 (Jan.-Mar. 2017).
Uhmann, et al., "Antitumoral Effects of Calcitriol in Basal Cell Carcinomas Involve Inhibition of Hedgehog Signaling and Induction of Vitamin D Receptor Signaling and Differentiation," *Mol. Cancer Ther.* 10(11):2179-2188 (Nov. 2011).
Valentine, et al., "Fibrodysplasia Ossificans Progressiva in the Cat," *J. Vet. Int. Med.* 6(6):335-340 (Nov. 1992).
Vilar, et al., "Kinematic characteristics of myositis ossificans of the semimembranosus muscle in a dog," *Can. Vet. J.* 51(3):289-292 (Mar. 2010).
Wang, et al., "Bone Morphogenetic protein-2 exhibits therapeutic benefits for osteonecrosis of the femoral head through induction of cartilage and bone cells," *Exp. Ther. Med.* 15(5):4298-4308 (May 2018).
WANG, et al, "Identification of the Vitamin D Receptor in Osteoblasts and Chondrocytes But Not Osteoclasts in Mouse Bone," *J. Bone Miner. Res.* 29(3):685-692 (Mar. 2014).
Warren, et al., "Fibrodysplasia Ossificans in Three Cats," *Vet. Pathol.* 21(5):495-499 (Sep. 1994).
Wozney, et al., "Novel regulators of bone formation: molecular clones and activities," *Science* 242(4885):1528-1534 (Dec. 1988).
Xu, et al., "Tissue source determines the differentiation potentials of mesenchymal stem cells: a comparative study of human mesenchymal stem cells from bone marrow and adipose tissue," *Stem Cell Research & Therapy* 8:275 pp. 1-11 (2017)
Yabuzoe, et al., "Fibrodysplasia Ossificans Progressiva in a Maine Coon Cat with Prominent Ossification in dorsal Muscle," *J. Vet. Med. Sci.* 71(12):1649-1652 (Dec. 2009).
Zhang, et al., "Structural Basis for Cholesterol Transport-like Activity of the hedgehog Receptor Patched," *Cell* 175(5):1352-1364 (Nov. 2018).
Gvozdenović-Jeremić, et al., "Antiosteogenic effect of arsenic trioxide, cholecalciferol, lovastatin or their combination in vitro," *J. Serb. Chem. Soc.* 84(0):1-11 (2019).
Office Action dated Mar. 20, 2019 for continuation U.S. Appl. No. 16/279,421.
Response to Office Action dated Mar. 20, 2019 filed for continuation U.S. Appl. No. 16/279,421 on Jun. 14, 2019.
Terminal Disclaimer filed for continuation U.S. Appl. No. 16/279,421 on Jun. 14, 2019.
Notice of Allowance dated Jul. 5, 2019 for continuation U.S. Appl. No. 16/279,421.
Response filed with Request for Continued Examination filed for continuation U.S. Appl. No. 16/279,421 on Aug. 12, 2019.
Notice of Allowance dated Aug. 26, 2019 for continuation U.S. Appl. No. 16/279,421.

\* cited by examiner

COMPOSITIONS AND METHODS FOR PREVENTING AND TREATING HETEROTOPIC OSSIFICATION AND PATHOLOGIC CALCIFICATION

CROSS REFERENCE TO RELATED APPLICATIONS

The present application claims the benefit of U.S. provisional application 62/395,374, filed on Sep. 15, 2016, the contents of which is incorporated by reference herein in its entirety.

FIELD OF THE INVENTION

The present invention is directed to methods of preventing or treating heterotopic ossification and other forms of pathologic calcification in patients by administering drug combinations containing: a) an antagonist of the Hedgehog signaling pathway; b) vitamin D, cholecalciferol or a vitamin D analog; and/or c) a statin. It also includes pharmaceutical compositions administered to patients in the performance of these methods. The invention is also directed to methods of treatment or prevention which utilize vitamin D, cholecalciferol or a vitamin D analog in the absence of an Hh pathway antagonist or a statin; and which use a statin in the absence of an Hh pathway antagonist, vitamin D, cholecalciferol or a vitamin D analog.

BACKGROUND OF THE INVENTION

Heterotopic ossification (HO) is characterized by the formation of ectopic bone in soft tissues, such as the fibrous tissue adjacent to joints. It is most commonly associated with trauma, such as spinal cord injury, brain injuries, head injuries, burns, fractures, muscle contusions, combat-related trauma and surgery (especially joint arthroplasty). In addition, HO may occur in patients that are on neuromuscular blockade to manage adult respiratory distress syndrome and in patients with non-traumatic myelopathies. In rare cases, HO may present as part of a hereditary disease and is sometimes associated with lower motor neuron disorders. The consequences of HO may include, inter alia, joint contracture and ankylosis, pain, spasticity, swelling, fever, neurovascular compression, pressure ulcers, and significant disability. Lesions range from small, clinically insignificant foci to massive deposits throughout the body.

NSAIDs, such as indomethacin, can be effective in the prevention of HO if treatment is started early and preoperative radiation may be used to prevent HO after total hip or knee arthroplasty. Combined postoperative radiotherapy and indomethacin has also been suggested to be effective at preventing HO. Unfortunately both radiation therapy and NSAID treatment have significant limitations and may result in serious side effects (see Baird, et al., J. Ortho. Surg. Res. 4:12 (2009)).

There are currently no generally effective treatments for ectopic bone formation due to genetic diseases. Areas of well-circumscribed HO can sometimes be surgically removed with successful long-term results but resection of diffuse lesions usually leads to recurrences or complications. Successful functional repositioning of a joint after the development of a contracture from HO may also occasionally be possible. However, treatment options are very limited and these diseases are generally severely disabling.

Recent analyses have suggested that the cellular origin for ectopic bone formation may be mesenchymal progenitor cells. The differentiation of these cells into osteogenic lineages is induced by a pathological microenvironment in soft tissues outside the skeletal tissue, which includes inflammation. Recent reports suggest that drugs that act as antagonists of the Hedgehog signaling pathway (which is essential for proper embryonic development and is believed to play a role in the development of some cancers) may be effectively used to prevent or treat HO as well as other pathological conditions characterized by ectopic calcification (see e.g., US 2014/0220154). Further development of treatment methods using Hh pathway antagonists and other agents is clearly warranted.

SUMMARY OF THE INVENTION

The present invention is based on the concept that vitamin D, cholecalciferol, vitamin D analogs; and statins can be used to inhibit osteogenesis in mesenchymal stem cells and to prevent or treat heterotopic ossification, vascular calcification, or pathologic calcification in a patient. It is further based on the concept that combinations of these agents, and combinations of these agents together with Hedgehog (Hh) pathway antagonists, can produce a greater effect in functional assays of osteogenesis prevention than agents used alone. Effects may include changes in gene expression and a reduction in alkaline phosphatase (AP) activity, a sign of prevented cell differentiation and HO aversion. As AP gene expression correlates with osteogenesis, the drugs and drug combinations discussed herein are believed to be effective in decreasing the cascade leading to HO and to act in a dose-dependent and synergistic manner. This may allow one to optimize the safety profile of a treatment by minimizing the individual agent's quantity and thus reducing toxicity associated with high doses of compounds. Treatment should be especially effective in those patients in which HO is associated with aberrant Hh signaling activity.

In its first aspect, the invention is directed to a method for inhibiting osteogenesis in mesenchymal stem cells, by contacting the cells with:
 a) a combination of a Hedgehog (Hh) pathway antagonist together with:
  i) vitamin D, cholecalciferol or a vitamin D analog; or
  ii) a statin;
 b) a combination of:
  i) vitamin D, cholecalciferol or a vitamin D analog; and
  ii) a statin; or
 c) a combination of:
  i) a Hh pathway antagonist;
  ii) vitamin D, cholecalciferol or a vitamin D analog; and
  iii) a statin.

In all of the combinations, the compounds are administered to cells in a co-timely manner, preferably concomitantly and more preferably, essentially simultaneously. The dosage of each compound should be sufficient to make the combination effective at inhibiting osteogenesis. Also, the combination in paragraphs a), b) or c) should produce a greater degree of inhibition than any components of the combination can produce when used in the absence of all of the components. The most preferred of the combinations contains all three of: i) an Hh pathway antagonist; ii) vitamin D, cholecalciferol or a vitamin D analog; and iii) a statin.

The invention is also directed to a method for preventing or treating heterotopic ossification, vascular calcification, or other pathologic calcification in a patient, by administering any of the combinations set forth above. These agents should be administered in a co-timely manner (i.e., a therapeutically effective amount of a first drug should be present in the patient when the second drug is given and, if a third drug is given, then both a therapeutically effective amount of the first drug and a therapeutically effective amount of the second drug should be present when the third drug is administered). Preferably the drugs are administered concomitantly (within one hour of one another) and still more preferably, essentially simultaneously (within five minutes of one another) or in a single unit dosage form. The dosage of the compounds given to patients should be sufficient to make the combination therapeutically effective and, preferably the combination of drugs should be more effective at preventing or treating heterotopic ossification, vascular calcification, or other pathologic calcification in a patient, than any single component of the combination when administered in the absence of the other components. The most preferred combination has all three of: i) an Hh pathway antagonist; ii) vitamin D, cholecalciferol or a vitamin D analog; and iii) a statin.

This treatment may be used for patients with ectopic bone formation or calcification of any origin, including spinal cord damage, traumatic injuries, head and brain injuries, burns, bone fractures, muscle injuries, and surgery. It should also be effective in patients with diseases or conditions that predispose them to ectopic bone formation or calcification, such as atherosclerosis or myocardial infarction, and in genetic diseases such as osseous heteroplasia, fibrodysplasia ossificans progressiva and Albright's hereditary osteodystrophy.

The dosage administered to a patient will vary depending on the particular agents being administered, the route of administration and clinical factors unique to the individual being treated. As a guide however, it is expected that, when administration is by an oral or transdermal route, patients will typically receive a combination of 1-500 mg/day of an Hh pathway antagonist; 300-3000 IU/day of vitamin D, cholecalciferol or a vitamin D analog; and/or 1-500 mg/day of a statin. Similar dosages may also be used for systemic or local injection but, in these instances, it may be possible to reduce the dosage somewhat (e.g., by 20-80%). These dosages apply regardless of which combination is administered to a patient.

An Hh pathway antagonist may be an inhibitor of mesenchymal stem cells and, structurally, may take the form of a protein or peptide ligand that binds to the Sonic receptor and prevents activation, an antibody that binds to either Sonic, Desert or Indian or to the receptor for these ligands, or an siRNA that inhibits the expression of one or more genes activated by the Hh pathway. Specific Hh pathway antagonists that may be used in compositions include: a) zerumbone epoxide; b) staurosporinone; c) 6-hydroxystauro-sporinone; d) arcyriaflavin C; e) 5,6-dihydroxyarcyriaflavin A; f) physalin F; g) physalin B; h) cyclopamine; i) HPI-1, HPI-2; HPI-3; or HPI-4; j) arsenic trioxide (ATO); k) sodium arsenite; l) phenylarsine; m) GANT-58; n) GANT-61; o) zerumbone; and p) inhibitors of the expression of the genes Ptch1, Gli1 or HIP. Of these the most preferred is arsenic trioxide (ATO) administered at a dose of 0.05 to 0.20 mg/kg/day, and more preferably at 0.10 to 0.20 mg/kg/day. Preferred combinations also include vitamin D or cholecalciferol and a statin selected from the group consisting of: Atorvastatin; Fluvastatin; Pravastatin; Rosuvastatin; Simvastatin; Pitavastatin; Cerivastatin; Lovastatin; and Mevastatin.

Overall, a particularly preferred method of preventing or treating heterotopic ossification, vascular calcification, or pathologic calcification in a patient, includes the co-timely (and more preferably concomitant or essentially simultaneous) administration of: a) an Hh pathway antagonist selected from the group consisting of: zerumbone epoxide; staurosporinone; 6-hydroxystauro-sporinone; arcyriaflavin C; 5,6-dihydroxyarcyriaflavin A; physalin F; physalin B; cyclopamine; HPI-1, HPI-2; HPI-3, or HPI-4; arsenic trioxide; sodium arsenite; phenylarsine; GANT-58; GANT-61; zerumbone; and inhibitors of the expression of the genes Ptch1, Gli1 or HIP, with the most preferred being arsenic trioxide; b) vitamin D or cholecalciferol; and c) a statin selected from the group consisting of Atorvastatin; Fluvastatin; Pravastatin; Rosuvastatin; Simvastatin; Pitavastatin; Cerivastatin; Lovastatin; and Mevastatin.

The dosage of each compound should be sufficient to make the overall treatment therapeutically effective and preferably synergistic. In the context used herein, the term "synergistic" means that the effect of a combination of drugs is greater than the maximum effect that can be achieved when the drugs are used individually. For example, the combination of ATO, cholecalciferol and levostatin would be acting synergistically with respect to preventing heterotopic ossification after surgery if, compared to an untreated group, fewer people developed ectopic ossification when given the combination then when administered any one component of the combination alone. When used to treat existing ectopic ossification, synergism may occur with respect to one or more symptoms associated with ossification such as pain, swelling, range of joint motion etc. Synergism may also manifest itself in other ways, such as the rapidity with which relief from a symptom is first experienced, or the duration of action.

In addition, the treatment methods described herein and the compositions used to accomplish those methods, may exhibit a reduction in the frequency or severity of one or more side effects relative to that produced by administering one of the components alone. Specific side effects may be reduced include weakness, fatigue, drowsiness, headache, loss of appetite, dry mouth, metallic taste, nausea, vomiting, liver damage, kidney failure, rhabdomyolysis, pleural effusion, fever, palpitations, tachycardia, weight gain, dyspnea, leukocytosis, prolonged qt interval on ECG, and cardiac arrhythmia.

In another aspect, the invention is directed to a pharmaceutical composition in unit dosage form, which includes any of the combinations set forth above. These agents should be present in an amount such that they are therapeutically effective upon the administration of one or more unit dosage forms to a patient. Although only two agents may be present, it is preferred that all three be included in a single unit dosage form.

For dosage forms designed for oral delivery (e.g., pills, tablets or capsules) or for transdermal delivery (e.g., patches, gels, foams or ointments), the Hh antagonist should typically be present in the compositions in an amount of 1-500 mg; vitamin D, cholecalciferol or a vitamin D analog should be present at 100-3000 IU; and the statin should be present at 1-500 mg. The most preferred composition has ATO at 1-100 mg; cholecalciferol at 100-3000 IU; and a statin selected from Atorvastatin; Fluvastatin; Pravastatin; Rosuvastatin; Simvastatin; Pitavastatin; Cerivastatin; Lovastatin; and Mevastatin.

Dosage forms for injection are essentially the same as those for oral delivery and comprise: an Hh antagonist at 1-500 mg; vitamin D, cholecalciferol or a vitamin D analog at 300-3000 IU; and a statin at 1-500 mg. However somewhat lower amounts may also be possible. Thus, a dosage forms designed for local or systemic injection (or for implantation) may have an Hh antagonist present at 0.1-50 mg; vitamin D or cholecalciferol present at 100-3000 IU or an equivalent amount of a vitamin D analog; and a statin at 0.1-50 mg. Specifically preferred components are the same as for oral compositions.

The Hh antagonist used in compositions may be an inhibitor of mesenchymal stem cell differentiation and may take the form of protein or peptide ligand that binds to the Sonic receptor and prevents activation; an antibody that binds to either Sonic, Desert or Indian or to the receptor for these ligands; or an siRNA that inhibits the expression of one or more genes activated by the Hh pathway. The most preferred compositions will be in the form of a pill, tablet or capsule for oral administration or a patch, gel, foam or ointment for topical administration, and comprise: a) 1-500 mg of an antagonist of the Hh pathway; (b) 100-3000 IU of vitamin D or cholecalciferol; and c) 1-500 mg of a statin. The Hh pathway antagonist may be any of those recited herein but will most preferably be arsenic trioxide at 5-50 mg. The most preferred statin is selected from the group consisting of: Atorvastatin; Fluvastatin; Pravastatin; Rosuvastatin; Simvastatin; Pitavastatin; Cerivastatin; Lovastatin; and Mevastatin.

The invention also includes a method for manufacturing a sterile pharmaceutical formulation comprising a) arsenic trioxide; and b) vitamin D or cholecalciferol. This is accomplished by: (a) solubilizing arsenic trioxide in an aqueous solution at a pH greater than 10; (b) neutralizing the arsenic trioxide solution with an acid to a pH between 8 and 10; (c) diluting the arsenic trioxide solution from step (b) in a pharmaceutical carrier that stabilizes it and lowers the pH to about 7 (e.g., from 6.8 to 7.2); (d) emulsifying the arsenic trioxide with vitamin D, cholecalciferol or a vitamin D analog; and (e) sterilizing the pharmaceutical composition. If desired, one or more statins may be substituted for the vitamin during emulsification or may be included as a third component.

All of the pharmaceutical compositions may be used in the prevention or treatment of heterotopic ossification, vascular calcification, or pathologic calcification according to the methods and dosages described herein.

The present invention is also directed to a method for inhibiting osteogenesis in mesenchymal stem cells and to a method for preventing or treating heterotopic ossification, vascular calcification, or other pathologic calcification in a patient, by administering vitamin D, cholecalciferol or a vitamin D analog in the absence of a Hh pathway antagonist or a statin; and by administering a statin in the absence of a Hh pathway antagonist or any of vitamin D, cholecalciferol or a vitamin D analog. Specific statins that may be used include: Atorvastatin; Fluvastatin; Pravastatin; Rosuvastatin; Simvastatin; Pitavastatin; Cerivastatin; Lovastatin; and Mevastatin.

Treatment of patients may be for ectopic bone formation or calcification of any origin, including spinal cord damage, traumatic injuries, head and brain injuries, burns, bone fractures, muscle injuries, and surgery. The agents should also be effective in patients with diseases or conditions that predispose them to ectopic bone formation or calcification, such as atherosclerosis or myocardial infarction, and in genetic diseases such as osseous heteroplasia, fibrodysplasia ossificans progressiva and Albright's hereditary osteodystrophy.

In all cases, patients should receive a therapeutically effective amount of a drug. It is expected that, when administration is by an oral or transdermal route, patients will typically receive 300-3000 IU/day of vitamin D, cholecalciferol or a vitamin D analog; or 1-500 mg/day of a statin. Similar dosages may also be used for systemic or local injection but, typically they will be reduced, e.g., by 20-80%.

DETAILED DESCRIPTION OF THE INVENTION

A. Definitions

Figure 1:
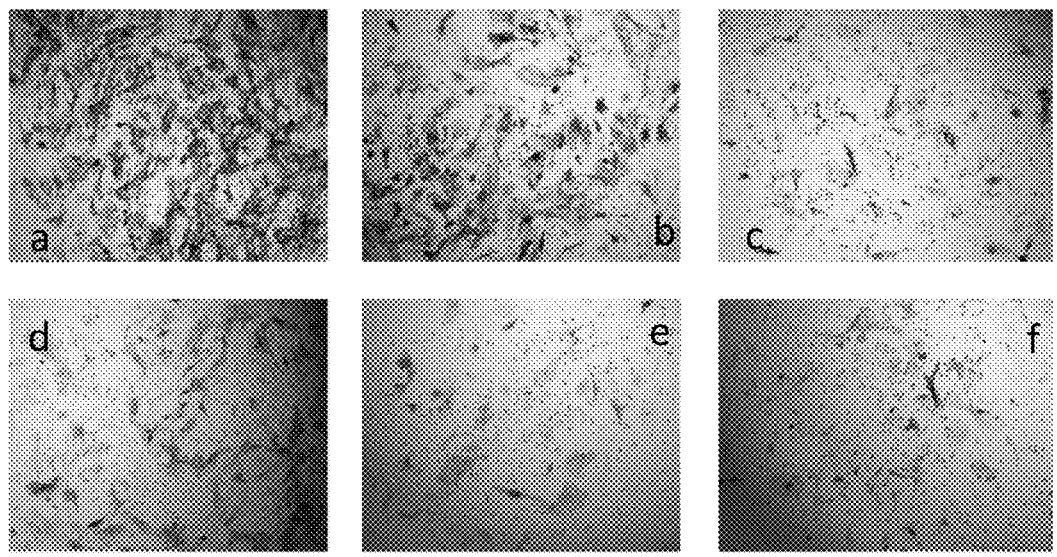
FIG. 1: Alkaline phosphatase assay of primary BMSC, (P1) isolated from wild type mice: a) Control, no agent present; b) Arsenic trioxide (ATO), 10 μM present during osteogenesis; c) Cholecalciferol 10 μM present in media during osteogenesis; d) Lovastatin 104 present in media during osteogenesis; e) NP101 present during osteogenesis diluted (1:1) f) NP101 present during osteogenesis diluted (1:10).

Administration: As used herein this term refers both to drugs given to a patient by health care personnel (e.g., a physician or nurse) as well to self administration, i.e., patients taking medication themselves.

Co-timely Administration: As used herein, "co-timely administration" means administration of a subsequent drug to prevent or treat heterotopic ossification, vascular calcification, or pathologic calcification during the time when a previously administered, first drug is still present in an amount in a patient that is therapeutically effective in combination with the second drug. Thus, drugs must be given in close enough temporal proximity that they can have a cumulative effect. If a third drug is given, then this must be done while both the first and second drugs are present in therapeutically effective amounts when in combination with the third.

Concomitant Administration: As used herein, the term "concomitant administration" means that drugs are given within one hour of one another.

Essentially Simultaneous Administration: As used herein this phrase refers to drugs that are given in a single unit dosage form or which are given within 5 minutes, and preferably 2 minutes of one another Heterotopic Ossification: Heterotopic ossification is the deposition of bone at sites in the body where it does not belong. Unless otherwise indicated, the term as used herein refers to bone formation at an abnormal site wherever that site happens to be and regardless of the cause.

Vascular calcification: Vascular calcification refers to the deposition of calcium in blood vessel structures and is often associated with atherosclerosis. (Bostrom, et al., *J. Clin. Invest.* 91:1800-09 (1993)). The consequences of calcification of blood vessels can be severe and may lead to congestive heart failure, aortic stenosis and weakened vasomotor responses.

Pathologic Calcification: For the purposes herein, pathologic calcification may be considered to be the deposition of calcium salts in soft tissue causing a hardening, but not bone formation. Thus, the term includes vascular calcification but also includes calcification outside of the vasculature.

Vitamin D, Cholecalciferol and Vitamin D Analogs: As used herein "cholecalciferol" refers specifically to vitamin D3 whereas the term "vitamin D" comprises all forms of vitamin D (including vitamin D2 (ergocalciferol) and D3 (cholecalciferol)) and combinations of these forms. Unless otherwise indicated, dosages or quantities recited refer to the total combined amount of all forms of vitamin D administered to a patient or present in a composition. The term "vitamin D analog refers to any compound (other than a naturally occurring human form of vitamin D) which has vitamin D biological activity and especially any such compound that binds to, and activates the vitamin D receptor (i.e., the calcitrol receptor). Such receptors may be found, for example in human osteoblasts, hepatocytes or immune cells. Examples of vitamin D analogs include but are not limited to those in the following US patent references (all of which are incorporated by reference herein in their entirety): (U.S. Pat. Nos. 7,985,744; 8,198,263; 7,659,421; 7,211,680; 7,115,758; 7,112,579; 7,074,777; 6,538,145; 6,359,152; 6,277,837; 6,124,276; 6,043,385; 6,013,814; 5,945,410; 5,756,733; 5,700,791; 5,665,716; 5,446,035; 5,232,836; 4,891,364; 4,857,518 4,851,400).

Statins: Statins are recognized in the art as a distinct drug class that act as inhibitors of 3-hydroxy-3-methylglutaryl coenzyme A reductase (HMG-CoA reductase), an enzyme involved in the synthesis of cholesterol. Structurally, they are characterized by a dihydroxyheptanoic acid group (sometimes in the form of a lactone) which forms a structure resembling HMG-CoA (the substrate of HMG-CoA reductase). This group is attached to a variety of ring systems (including aromatic, heterocyclic or aromatic-heterocyclic, unsubstituted or substituted, mono-, di- or poly-cyclic ring systems). Specific examples of statins include Atorvastatin; Fluvastatin; Pravastatin; Rosuvastatin; Simvastatin; Pitavastatin; Cerivastatin; Lovastatin; and Mevastatin. These specific compounds and all compounds recognized in the art as being a member of the statin drug class are included within the scope of the invention.

Hedgehog pathway antagonists: The hedgehog signaling pathway is involved in the differentiation of cells during embryonic development and also appears to play a role regulating adult stem cells. Inhibition of this pathway has been reported to decrease the proliferation and clonogenicity of human mesenchymal stem cells which are known to be capable of differentiating into, inter alia, osteoblasts (see Plaisant, et al., *PLoS One:* 6(2):e16798 (2011)). Any inhibitor of this pathway identified in the art as being effective in humans is within the scope of the invention regardless of its mechanism of action. This includes: small molecules that block the binding of a hedgehog ligand (Desert, Indian or Sonic) to its receptor; antibodies that target either ligand or receptor; agents that block intracellular activation after receptor binding; and agents that block gene expression such as siRNAs. Examples of specific inhibitors include: a) zerumbone epoxide; b) staurosporinone; c) 6-hydroxystaurosporinone; d) arcyriaflavin C; e) 5,6-dihydroxyarcyriaflavin A; f) physalin F; g) physalin B; h) cyclopamine; i) HPI-1, HPI-2; HPI-3; or HPI-4; j) arsenic trioxide (ATO); k) sodium arsenite; l) phenylarsine; m) GANT-58; n) GANT-61; o) zerumbone; and p) inhibitors of the expression of the genes Ptch1, Gli1 or HIP. Examples of other Hh pathway antagonists that may be used in the invention include, but are not limited, to those in the following US patent references (all of which are incorporated by reference herein in their entirety): U.S. Pat. No. 9,427,431; 9,409,871; 9,346,791; 9,345,699; 9,321,761; 9,278,961; 9,216,964; 9,174,949; 9,173,869; 9,149,527; 9,096,686; 9,073,835; 9,000,023; 8,835,648; 8,802,639; 8,778,927; 8,759,367; 8,530,456; 8,486,400; 8,410,601; 8,273,747; 8,101,610; 8,030,454; 7,741,298; 7,407,967; 6,683,108; and 6,291,516.

Therapeutically effective amount: The term "therapeutically effective amount" means a dosage of drug that provides the specific pharmacological response for which the drug is administered in a significant number of subjects in need of such treatment. With respect to the therapeutic agents discussed herein, this would be a dose of each active drug which, in combination (or in the case of vitamin D, cholecalciferol, a vitamin D analog or a statin, when used alone or in combination) reduces the number of patients developing heterotopic ossification (e.g., after arthroscopic surgery, spinal injury, trauma, head or brain injuries, bone fractures or burns) by at least 15% (preferably at least 30% and more preferably at least 50%) relative to clinically matched patients that are not treated. In patients that are diagnosed as having heterotopic ossification, a therapeutically effective amount is a dosage sufficient to reduce the clinical symptoms associated with the condition to a greater degree in at least 15% of patients receiving treatment (preferably at least 30% and more preferably at least 50%) relative to clinically matched patients that are not treated. This reduction in symptoms should occur in less than one year after treatment is begun and generally in less than one month. In most cases, a reduction in symptoms should be seen in less than one week, and preferably within only a day or two, after treatment is initiated. Clinical symptom improvement may take the form of a greater reduction in pain, swelling, or pressure or a greater shrinkage of bone or calcium deposits. Note that reference to "specific pharmacological response for which the drug is administered in a significant number of subjects in need of such treatment" is a recognition that a "therapeutically effective amount," administered to a particular subject may not be effective in that patient even though such dosage is deemed to be therapeutically effective by those skilled in the art.

Unit dosage form: The term "unit dosage form" is defined as a single drug administration entity. By way of example, a single pill, tablet, capsule, dragee, or trochee, or a specified volume of solution for injection would be a unit dosage form. It also applies to a single dosage of drug applied transdermally in a patch or as part of a specified amount of gel, foam or ointment.

B. Compounds

Hedgehog inhibitors have been thoroughly described in the literature and have generated interest as potential therapies for cancer. Vitamin D, cholecalciferol and vitamin D analogs and methods for obtaining these compounds are also described in the literature as are statins. Since all of these compounds are well known, one of skill in the art will be able to either purchase them or make them using information in the literature and standard laboratory methods.

C. Drug Formulation and Dosage Forms

The compounds described herein may be administered to patients in a pharmaceutical composition comprising the compounds along with a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art (see, e.g., *Remington's Pharmaceutical Sciences,* 16th edition, E. W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; and antioxidants.

Although dosage forms for oral delivery are preferred, the invention is compatible with the delivery of compounds by any route known in the art, including peroral, internal, rectal, nasal, lingual, transdermal, intravenous, intra-arterial, intramuscular, intraperitoneal, intracutaneous and subcutaneous routes. Liquid dosage forms for oral administration include, but are not limited to, pharmaceutically acceptable emulsions, microemulsions, solutions, suspensions, syrups and elixirs. In addition to the active compounds, liquid dosage forms may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters.

Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present.

The most preferred dosage forms are forms such as capsules, tablets and pills. In these dosage forms, the active compound will typically be mixed with at least one inert, pharmaceutically acceptable excipient or carrier such as sodium citrate, or dicalcium phosphate and/or: fillers or extenders such as starches, lactose, sucrose, glucose, mannitol and silicic acid; binders such as, for example, carboxymethyl cellulose, alginates, gelatin, polyvinylpyrrolidinone, and acacia, humectants such as glycerol; disintegrating agents such as calcium carbonate, silicates or sodium carbonate; solution retarding agents such as paraffin; absorption accelerators such as quaternary ammonium compound; wetting agents such as cetyl alcohol or glycerol monostearate; absorbents such as kaolin; and lubricants, such as talc, magnesium stearate; sodium lauryl sulphate, etc. In addition, dosage forms may include buffering and flavoring agents.

D. Dosage

Pharmaceutical compositions will typically be given to a patient in one or more unit dosage forms that alone or together provide a dose that is therapeutically effective. The exact amount of each active drug in formulations will vary depending on the specific drugs chosen and the route of administration. In general, the dosage of Hh inhibitor given orally will be about 1-500 mg daily, but higher or lower dosages may be used by physicians depending on the response of individual patients. Similar dosages would apply to transdermal formulations including those delivered using a transdermal patch or those in the form of a gel, foam or ointment. In the most preferred embodiment, arsenic trioxide is used as the Hh antagonist and is administered to patients at a dosage of about 0.15 mg/kg/day. If injected, the dosage may be essentially the same as for oral administration but it may also be possible to reduce the dosage by 20 to 80% or more.

The dosage of statin will be between 1 and 500 mg (and usually 1 to 100 mg), given orally or transdermally per day. Again, if injected this may be reduced by 20 to 80% or more.

In oral and transdermal formulations, the amount of vitamin D or cholecalciferol will typically be about 300-3000 IU per day. If an analog is used, an amount of drug equivalent to 300-3000 IU of D3 may be used initially and adjusted according to patient response. If injected this may be reduced by 20 to 80%.

E. Treatment Methods

Subjects receiving therapeutic agents according to the methods described herein will fall into two categories. The first consists of individuals that do not yet have abnormal bone formation or calcification but are part of a group recognized as being prone to this occurring. Included in this group are patients that have undergone surgery (particularly arthroscopic surgery of a hip or other joint), and those that have undergone traumatic injuries, fractures, wounds, head or brain injuries and burns. The group also includes subjects with atherosclerosis, that have had a myocardial infarction or that have a genetic disease associated with ectopic bone formation or calcification. The objective in these cases is to reduce the likelihood of HO or abnormal calcification occurring. In general, these patients will receive daily dosages that continue until the attending physician is satisfied that increased risk has subsided. This may be anywhere from a few weeks up to several years. In the case where increased risk of heterotopic ossification, vascular calcification, or pathologic calcification is due to genetic factors or ongoing disease, administration may be continued for the life of the patient.

The second category of patients will be those that have been identified clinically as already suffering from heterotopic ossification, or pathologic calcification and for whom the objective is primarily to treat the existing condition. In general, these patients will be administered compositions in the same manner as those in which the objective is prevention but dosages and dosing schedules may be varied depending on the degree to which a response is observed and may be combined with physical therapy or surgery.

In all cases, treatment may be altered by physicians based on clinical factors unique to individual patients.

Examples

This example, is concerned with the effect of certain combinations of compounds on mesenchymal stem cells and bone marrow stromal cells osteogenic differentiation.

Methods

Mesenchymal Stem Cells Isolation:

Bone marrow stromal cells were isolated from six to eight weeks old wild type mice. Femurs and tibias were dissected from surrounding tissues. The epiphyseal growth plates were removed and the marrow was collected by flushing with modified essential medium (MEM) containing 100 U/ml Penicillin, 100 μg/ml streptomycin and 10% fetal bovine serum with a 25 G needle. Single cell suspensions were prepared by passing the cell clumps through an 18 G needle followed by filtration through a 70-μm cell strainer.

An aliquot of cells was diluted 1:1 with 0.04% trypan blue in PBS and viable cells were plated at a density of $2\times10^6$ cells/cm$^2$ and in a 35-mm culture dish and exposed to recombinant mouse Prolactin (PRL) (1 ng/ml) and/or Lacritin 2(LCN2) (18 ng/ml) in Alpha MEM media with 20% FBS, L-Glutamine 2 mM and Pen-Strep (1×) for three passages to prime cells for osteogenesis. After the third passage, 50,000 bone marrow stromal cells per well were plated in a 24 well plate in Alpha MEM 20% FBS, L-Glutamine (4 mM), PenStrep (1×) and MEM Non-Essential Amino Acids (1×).

After cells reached confluence, medium was replaced with osteogenic differentiation medium (OM). Osteogenic differentiation medium (OM) consists of: DMEM, 10% FBS, Pen-Strep (1×), L-Glutamine (2 mM), 10 mM beta glycerol phosphate and 50 µg/ml ascorbic acid. Duplicate wells were exposed to differentiation media without any agent (control), single agent (Cholecalciferol, ATO or Lovastatin) or Nosto-101 combination agents. Media replacement occurred every 2-3 days with fresh differentiation medium (made each time during feeding) with or without single agent or Nosto-101.

Alkaline Phosphatase Assay:

Cells were stained after 4 days exposure in OM differentiation medium for Alkaline Phosphatase (AP) assay. This is a colorimetric assay in which NBT (nitro-blue tetrazolium chloride) and BCIP (5-Bromo-4-chloro-3'-indolyphosphate p-toluidine salt) yields insoluble purple precipitate when reacted with alkaline phosphatase enzyme.

After 4 days of culturing cells in OM media, cells were fixed with 4% paraformaldehyde and then washed once with PBS. One ml of One-step NBT/BCIP staining solution (Thermo Fisher) was added per well and the cells were then incubated in the dark for 30 min to 1 h and checked for color development. The reaction was quickly stopped by removing NBT/BCIP and adding water.

ATO:

Arsenic trioxide stock solution was prepared by placing 50 mg of ATO (Sigma) at the bottom of a 50 ml conical tube and dissolving it with 1 ml of 1M NaOH. 48 ml of PBS was then added and 1N HCl was used to adjust the pH to 7.2

Cholecalciferol (Sigma) was dissolved in absolute ethanol in 10 mM stock concentration. Working concentration used in cell culture experiments was 1004.

Lovastatin (Calbiochem) was dissolved in absolute ethanol in 1 mM stock concentration. Working concentration used in cell culture experiment was 1 µM.

NP 101 Formulation:

NP101 was prepared by mixing 10 µM ATO, 10 µM Cholecalciferol and 1 µM Lovastatin into a single mix by mixing it immediately with osteogenic media (OM).

qRT-PCR: Total RNA was isolated first with Trizol (Invitrogen) and then with RNeasy Kit (Qiagen). First strand cDNA was generated using a High capacity cDNA reverse transcriptase kit (Abcam). qPCR was performed using a Biorad cycler at 40 cycles of 95° C. for 5 seconds and at 60° C. for 30 seconds. PCR product was detected using Sybr-Green (BioRad). Primers used for amplifications were Actin: Forward 5'-CAC AGC TTC TTT GCA GCT CCT-3' (SEQ ID NO:1), Reverse 5'-CGT CAT CCA TGG CGA ACT G-3' (SEQ ID NO:2); Alk Phos: Forward 5'-CAC GCG ATG CAA CAC TCA GG-3' (SEQ ID NO:3), Reverse 5'-GCA TGT CCC CGG GCT CAA AGA-3' (SEQ ID NO:4).

Results

Relevant in vitro validations were performed for candidates like Arsenic Trioxide (ATO), Vitamin D and statins as single agents present during osteogenesis and NP101 as a combination of agents for comparison. For a functional assay an alkaline phosphatase (ALP) assay was used, as ALP is one of the very first enzymes active at the early stages of osteogenesis. A key to understanding the role of ALP in mineralization is provided by studies of the phased expression of genes during osteoblastic differentiation and growth plate cartilage calcification. In both tissues, bone and calcifying cartilage, ALP must function early in the process of osteoblast formation. Osteoblasts are integral to the formation of heterotopic bone through production of alkaline phosphatase (AP).

Bone marrow stromal cells isolated from wild type mice and plated at first passage (P1) were used to test osteogenic properties in the presence of ATO, cholecalciferol, lovastatin or NP101. An assay of alkaline phosphatase, a widely recognized biochemical marker for osteoblast activity was utilized as a comparison tool. Alkaline phosphatase activity is clearly present in control BMSC cells, without any agent, after only four days in osteogenic media. Based on the number of blue colored cells present in wells treated with OM and supplemented with ATO, Cholecalciferol, lovastatin or NP101, it was found that the alkaline phosphatase activity decreases if agent is present (FIG. 1).

Similar results were obtained with respect to alkaline phosphatase gene expression levels (Table 2). Compared to control (no agent present), all single agents an NP101 suppress alkaline phosphatase gene expression significantly, and up to 90%.

TABLE 2

The expression of a differentiation marker, Alkaline Phosphatase in BMSC culture after four days supplementation of OM media without (control) agents present, with single agents or NP101 calculated using $\Delta \Delta$ Ct method

| | Control (no agent present) | ATO, 10 µM | Cholecalciferol, 10 µM | Lovastatin, 1 µM | NP 101, 2× diluted | NP 101, 10× diluted |
|---|---|---|---|---|---|---|
| ALP gene expression fold change | 1.00 | 0.105 ± 0.01 | 0.350 ± 0.02 | 0.316 ± 0.02 | 0.156 ± 0.02 | 0.500 ± 0.075 |

Figure 2:
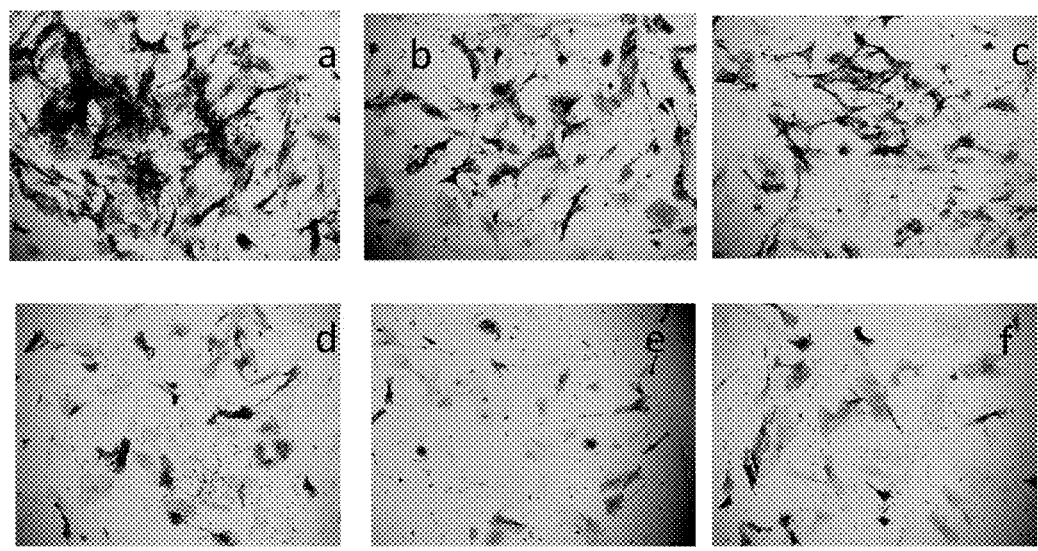
FIG. 2: Alkaline phosphatase assay of BMSC isolated from wild type mice and primed for osteogenesis; a) Control, no agent present; b) ATO, 10 μM present during osteogenesis; c) Cholecalciferol 1004 present in media during osteogenesis; d) Lovastatin 1 μM present in media during osteogenesis; e) NP101 present during osteogenesis diluted (1:1) f) NP101 present during osteogenesis diluted (1:10).

The effect of NP101 was explored in cells primed for osteogenesis, and having a higher expression profile of bone related markers than control. Recent study suggests that BMSC cells pretreated with Lacritin 2 (LCN2) and Prolactin (PRL) express higher mRNA levels of bone related markers and calcium deposits than control (cells without pretreatment). BMSC cells were primed for osteogenesis and then exposed to osteogenic media supplemented with single or combined agents (FIG. 2). Treatment with single agents, like ATO, Cholecalciferol or lovastatin clearly diminish ALP activity in cells, while NP101 even in its diluted form has the most prominent effect on reducing alkaline phosphatase activity, based on presence of bluish/purple cells.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A method for inhibiting osteogenesis in mesenchymal stem cells, comprising contacting said mesenchymal stem cells with:
   a) a combination of a Hedgehog (Hh) pathway antagonist together with:
      i) vitamin D, cholecalciferol or a vitamin D analog; or
      ii) a statin; or
   b) a combination of:
      i) an Hh pathway antagonist;
      ii) vitamin D, cholecalciferol or a vitamin D analog; and
      iii) a statin;

wherein the compounds of paragraphs a) and b) are administered to cells in a co-timely manner, and wherein the dosage of each compound is sufficient to make the combination effective at inhibiting osteogenesis.

2. The method of claim 1, wherein the compounds of paragraphs a) and b) are administered concomitantly.

3. The method of claim 1, wherein the combination set forth in paragraph a or b) produces a greater degree of inhibition than any components of the combination can produce when used in the absence of all of the components.

4. A method for treating heterotopic ossification, vascular calcification, or other pathologic calcification in a patient, comprising: administering to said patient:
   a) a combination of a Hedgehog (Hh) pathway antagonist together with:
      i) vitamin D, cholecalciferol or a vitamin D analog; or
      ii) a statin;
   b) a combination of:
      i) vitamin D, cholecalciferol or a vitamin D analog; and
      ii) a statin; or c) a combination of:
   i) a Hh pathway antagonist;
   ii) vitamin D, cholecalciferol or a vitamin D analog; and
   iii) a statin;
wherein the compounds of paragraphs a), b) and c), are administered to the patient in a co-timely manner and wherein the compounds are present in an amount sufficient to make the combination effective at treating said heterotopic ossification, vascular calcification, or other pathologic calcification.

5. The method of claim 4, wherein the compounds of paragraphs a), b) and c), are administered concomitantly.

6. The method of claim 4, wherein said compounds are administered to a patient in a single unit dosage form.

7. The method of claim 4, wherein said method is used to treat a patient for heterotopic ossification subsequent to spinal cord damage, traumatic injury, head or brain injuries, burns, bone fractures, muscle injuries, or joint replacement surgery and a therapeutically effective amount of said compounds is administered to said patient.

8. The method of claim 4, wherein said method is used to treat heterotopic ossification resulting from progressive osseous heteroplasia, fibrodysplasia ossificans progressiva or Albright's hereditary osteodystrophy and a therapeutically effective amount of said compounds is administered to said patient.

9. The method of claim 4, wherein said Hh pathway antagonist is administered to said patient at 1-500 mg/day; said vitamin D, cholecalciferol or a vitamin D analog is administered at 300-3000 IU/day; and said statin is administered at 1-500 mg/ day.

10. The method of claim 9, wherein said compounds are administered to a patient in a single unit dosage form.

11. The method of claim 4, wherein said Hh pathway antagonist is a ligand that binds to the Sonic receptor and prevents activation; an antibody that binds to either Sonic, Desert or Indian or to the receptor for these ligands; or an siRNA that inhibits the expression of one or more genes activated by the Hh pathway.

12. The method of claim 4, wherein said Hh pathway antagonist is selected from the group consisting of: a) zerumbone epoxide; b) staurosporinone; c) 6-hydroxystauro-sporinone; d) arcyriaflavin C; e) 5,6-dihyroxyarcyriaflavin A; f) physalin F; g) physalin B; h) cyclopamine; i) HPI-1, HPI-2; HPI-3; or HPI-4; j) arsenic trioxide (ATO); k) sodium arsenite; l) phenylarsine; m) GANT-58; n) GANT-61; o) zerumbone; and p) inhibitors of the expression of the genes Ptch1, Gli1 or HIP.

13. The method of claim 4, wherein said Hh pathway antagonist is arsenic trioxide (ATO).

14. The method of claim 13, wherein ATO is administered to said patient at a dosage of between 0.05 to 0.20 mg/kg/day.

15. The method of claim 4, wherein said statin is selected from the group consisting of: Atorvastatin; Fluvastatin; Pravastatin; Rosuvastatin; Simvastatin; Pitavastatin; Cerivastatin; Lovastatin; and Mevastatin.

16. The method of claim 4, wherein the combination set forth in paragraph a), b) or c) is more effective at inhibiting heterotopic ossification, vascular calcification, or pathologic calcification in a patient than any components of the combination can produce when used in the absence of all of the components.

17. The method of claim 1, wherein, in accordance with paragraph a), said mesenchymal stem cells are contacted with a combination of an Hh pathway antagonist and vitamin D, cholecalciferol or a vitamin D analog.

18. The method of claim 1, wherein, in accordance with paragraph a), said mesenchymal stem cells are contacted with a combination of an Hh pathway antagonist and a statin.

19. The method of claim 1, wherein, in accordance with paragraph b), said mesenchymal stem cells are contacted with a combination of: an Hh pathway antagonist; vitamin D, cholecalciferol or a vitamin D analog; and a statin.

20. The method of claim 4, wherein, in accordance with paragraph a), said patient is administered a combination of an Hh pathway antagonist and vitamin D, cholecalciferol or a vitamin D analog.

21. The method of claim 20, wherein the Hh pathway antagonist and the vitamin D, cholecalciferol or vitamin D analog are administered in a single unit dosage form.

22. The method of claim 20, wherein the Hh pathway antagonist is administered to said patient at 1-500 mg/day; and vitamin D, cholecalciferol or vitamin D analog is administered to said patient at 300-3000 IU/day.

23. The method of claim 20, wherein said Hh pathway antagonist is selected from the group consisting of: a) zerumbone epoxide; b) staurosporinone; c) 6-hydroxystauro-sporinone; d) arcyriaflavin C; e) 5,6-dihyroxyarcyriaflavin A; f) physalin F; g) physalin B; h) cyclopamine; i) HPI-1, HPI-2; HPI-3; or HPI-4; j) arsenic trioxide (ATO); k) sodium arsenite; l) phenylarsine; m) GANT-58; n) GANT-61; o) zerumbone;
   and p) inhibitors of the expression of the genes Ptch1, Gli1 or HIP.

24. The method of claim 4, wherein, in accordance with paragraph a), said patient is administered a combination of an Hh pathway antagonist and a statin.

25. The method of claim 24, wherein the Hh pathway antagonist and the statin are administered in a single unit dosage form.

26. The method of claim 24, wherein said Hh pathway antagonist is administered to said patient at 1-500 mg/day and said statin is administered to said patient at 1-500 mg/day.

27. The method of claim 24, wherein:
   A) said Hh pathway antagonist is selected from the group consisting of: a) zerumbone epoxide; b) staurosporinone; c) 6-hydroxystauro-sporinone; d) arcyriaflavin C; e) 5,6-dihyroxyarcyriaflavin A; f) physalin F; g) physalin B; h) cyclopamine; i) HPI-1, HPI-2; HPI-3; or HPI-4; j) arsenic trioxide (ATO); k) sodium arsenite; l) phenylarsine; m) GANT-58; n) GANT-61; o) zerumbone; and p) inhibitors of the expression of the genes Ptch1, Gli1 or HIP; and
   B) said statin is selected from the group consisting of: Atorvastatin; Fluvastatin; Pravastatin; Rosuvastatin; Simvastatin; Pitavastatin; Cerivastatin; Lovastatin; and Mevastatin.

28. The method of claim 4, wherein, in accordance with paragraph b), said patient is administered a combination of vitamin D, cholecalciferol or a vitamin D analog and a statin.

29. The method of claim 28, wherein the vitamin D, cholecalciferol or vitamin D analog and the statin are administered to a patient in a single unit dosage form.

30. The method of claim 28, wherein the vitamin D, cholecalciferol or vitamin D analog is administered to the patient at 300-3000 IU/day and the statin is administered to said patient at 1-500 mg/ day.

31. The method of claim 28, wherein the said statin is selected from the group consisting of: Atorvastatin; Fluvastatin; Pravastatin; Rosuvastatin; Simvastatin; Pitavastatin; Cerivastatin; Lovastatin; and Mevastatin.

32. The method of claim 4, wherein, in accordance with paragraph c), said patient is administered a combination of: i) a Hedgehog (Hh) pathway antagonist; ii) vitamin D, cholecalciferol or a vitamin D analog; and c) a statin.

33. The method of claim 32, wherein: the Hh pathway antagonist; the vitamin D, cholecalciferol or vitamin D analog; and the statin are administered to a patient in a single unit dosage form.

34. The method of claim 32, wherein: the Hh pathway antagonist is administered to said patient at 1-500 mg/day; the vitamin D, cholecalciferol or vitamin D analog is administered to the patient at 300-3000 IU/day and the statin is administered to said patient at 1-500 mg/ day.

35. The method of claim 32, wherein:
A) said Hh pathway antagonist is selected from the group consisting of: a) zerumbone epoxide; b) staurosporinone; c) 6-hydroxystauro-sporinone; d) arcyriaflavin C; e) 5,6-dihyroxyarcyriaflavin A; f) physalin F; g) physalin B; h) cyclopamine; i) HPI-1, HPI-2; HPI-3; or HPI-4; j) arsenic trioxide (ATO); k) sodium arsenite; 1) phenylarsine; m) GANT-58; n) GANT-61; o) zerumbone; and p) inhibitors of the expression of the genes Ptch1, Gli1 or HIP; and
B) the statin is selected from the group consisting of: Atorvastatin; Fluvastatin; Pravastatin; Rosuvastatin; Simvastatin; Pitavastatin; Cerivastatin; Lovastatin; and Mevastatin.

36. A pharmaceutical composition in unit dosage form comprising:
a) a combination of a Hedgehog (Hh) pathway antagonist together with:
   i) vitamin D, cholecalciferol or a vitamin D analog; or
   ii) a statin; or
b) a combination of:
   i) an Hh pathway antagonist;
   ii) vitamin D, cholecalciferol or a vitamin D analog; and
   iii) a statin;
wherein the pharmaceutical composition comprises the compounds of either paragraph a) or paragraph b) along with a pharmaceutically acceptable carrier.

37. The pharmaceutical composition of claim 36, wherein, when administered to a patient, the amounts of the compounds of paragraph a) or paragraph b) are sufficient to provide the specific pharmacological response for which the compounds are administered.

38. The pharmaceutical composition of claim 37, wherein the specific pharmacological response is the inhibition of heterotopic ossification, vascular calcification, or other pathologic calcification in a patient.

39. The pharmaceutical composition of claim 36, wherein said unit dosage form comprises: an Hh antagonist at 1-500 mg; vitamin D, cholecalciferol or a vitamin D analog at 300-3000 IU; and/or a statin at 1-500 mg.

40. The pharmaceutical composition of claim 36, wherein said Hh pathway antagonist is selected from the group consisting of: zerumbone epoxide; staurosporinone; 6-hydroxystauro-sporinone; arcyriaflavin C; 5,6-dihyroxyarcyria-flavin A; physalin F;
physalin B; cyclopamine; HPI-1, HPI-2; HPI-3, or HPI-4; arsenic trioxide; sodium arsenite; phenylarsine; GANT-58; GANT-61; zerumbone; and inhibitors of the expression of the genes Ptch1, Gli1 or HIP.

41. The pharmaceutical composition of claim 36, wherein said statin is selected from the group consisting of: Atorvastatin; Fluvastatin; Pravastatin; Rosuvastatin;
Simvastatin; Pitavastatin; Cerivastatin; Lovastatin; and Mevastatin.

42. The pharmaceutical composition of claim 36, wherein in accordance with paragraph a), said pharmaceutical composition comprises a Hedgehog (Hh) pathway antagonist together with a statin.

43. The pharmaceutical composition of claim 36, wherein in accordance with paragraph a), said pharmaceutical composition comprises a Hedgehog (Hh) pathway antagonist together with vitamin D, cholecalciferol or a vitamin D analog.

44. The pharmaceutical composition of claim 36, wherein in accordance with paragraph b), said pharmaceutical composition comprises a Hedgehog (Hh) pathway antagonist; vitamin D, cholecalciferol or a vitamin D analog; and a statin.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Primer sequence

<400> SEQUENCE: 1
cacagcttct ttgcagctcc tt                                            22

<210> SEQ ID NO 2
<211> LENGTH: 19
<212> TYPE: DNA
<213> ORGANISM: Artificial Sequence
<220> FEATURE:
<223> OTHER INFORMATION: Primer sequence

<400> SEQUENCE: 2
cgtcatccat ggcgaactg                                                19

<210> SEQ ID NO 3
<211> LENGTH: 23
<212> TYPE: DNA
<213> ORGANISM: Artificial Sequence
<220> FEATURE:
<223> OTHER INFORMATION: Primer sequence

<400> SEQUENCE: 3
cacgcgatgc aacaccactc agg                                           23

<210> SEQ ID NO 4
<211> LENGTH: 21
<212> TYPE: DNA
<213> ORGANISM: Artificial Sequence
<220> FEATURE:
<223> OTHER INFORMATION: Primer sequence

<400> SEQUENCE: 4
gcatgtcccc gggctcaaag a                                             21
```